US009351141B2

(12) United States Patent
Jacobsen

(10) Patent No.: US 9,351,141 B2
(45) Date of Patent: May 24, 2016

(54) HEADSET COMPUTER WITH HANDSFREE EMERGENCY RESPONSE

(71) Applicant: Kopin Corporation, Westborough, MA (US)

(72) Inventor: Jeffrey J. Jacobsen, Hollister, CA (US)

(73) Assignee: Kopin Corporation, Westborough, MA (US)

( * ) Notice: Subject to any disclaimer, the term of this patent is extended or adjusted under 35 U.S.C. 154(b) by 109 days.

(21) Appl. No.: 13/945,270

(22) Filed: Jul. 18, 2013

(65) Prior Publication Data

US 2014/0031001 A1    Jan. 30, 2014

Related U.S. Application Data

(60) Provisional application No. 61/675,546, filed on Jul. 25, 2012.

(51) Int. Cl.

| A61B 5/00 | (2006.01) |
|---|---|
| G06F 3/01 | (2006.01) |
| G06F 3/042 | (2006.01) |
| H04M 1/05 | (2006.01) |
| H04M 1/60 | (2006.01) |
| H04M 1/725 | (2006.01) |

(Continued)

(52) U.S. Cl.
CPC .............. *H04W 4/22* (2013.01); *A61B 5/6803* (2013.01); *G02B 27/017* (2013.01); *G06F 3/012* (2013.01); *G06F 3/017* (2013.01); *G06F 3/0304* (2013.01); *G06F 3/0425* (2013.01); *H04M 1/05* (2013.01); *H04M 1/6058* (2013.01); *H04M 1/6066* (2013.01); *H04M 1/72536* (2013.01); *H04M 1/72538* (2013.01); *G02B 2027/014* (2013.01); *G02B 2027/0138* (2013.01); *G02B 2027/0187* (2013.01); *H04R 5/033* (2013.01)

(58) Field of Classification Search
CPC ............ H04M 1/6066; H04M 1/6058; H04M 1/72536; H04M 1/72538
See application file for complete search history.

(56) References Cited

U.S. PATENT DOCUMENTS

| 8,223,024 B1 | 7/2012 | Petrou |
|---|---|---|
| 2008/0284587 A1 | 11/2008 | Saigh et al. |

(Continued)

FOREIGN PATENT DOCUMENTS

| EP | 1 701 483 A1 | 9/2006 |
|---|---|---|
| EP | 1 887 770 A1 | 2/2008 |

(Continued)

OTHER PUBLICATIONS

Notification of Transmittal of the International Search Report and the Written Opinion of the International Searching Authority, or the Declaration, for International Application No. PCT/US2013/051045, dated Nov. 8, 2013, consisting of 13 pages.

(Continued)

*Primary Examiner* — Nam Huynh
(74) *Attorney, Agent, or Firm* — Hamilton, Brook, Smith & Reynolds, P.C.

(57) ABSTRACT

Operating conditions for a headset computer are used to detect a situation where an emergency response mode should be activated. In emergency response mode, the headset computer may then broadcast location, live (real time) audio and video/data streams, and record other information concerning a possible theft and/or other situation of interest to law enforcement and/or security services.

14 Claims, 5 Drawing Sheets

(51) Int. Cl.
    *H04R 5/033*     (2006.01)
    *H04W 4/22*     (2009.01)
    *G06F 3/03*     (2006.01)
    *G02B 27/01*     (2006.01)

(56) References Cited

U.S. PATENT DOCUMENTS

| | | | |
|---|---|---|---|
| 2009/0251409 | A1 | 10/2009 | Parkinson et al. |
| 2010/0039493 | A1* | 2/2010 | Chao et al. ............ 348/14.02 |
| 2010/0099461 | A1* | 4/2010 | Rahfaldt et al. ............ 455/557 |
| 2011/0187640 | A1 | 8/2011 | Jacobsen et al. |
| 2011/0213664 | A1 | 9/2011 | Osterhout |
| 2012/0052852 | A1* | 3/2012 | Goldman ............ 455/418 |
| 2012/0224040 | A1* | 9/2012 | Wang ............ G06K 7/1091 348/77 |

FOREIGN PATENT DOCUMENTS

| | | |
|---|---|---|
| EP | 2 109074 A1 | 10/2009 |
| WO | WO 2009/120984 A1 | 10/2009 |

OTHER PUBLICATIONS

Roberto Baldwin, Google Glass Anti-Theft Patent Detects Burgled Headset, Calls the Coppers [online], Jul. 17, 2012 [retrieved on Oct. 16, 2013] Retrieved from the Internate URL: http://www.wired.com/gadgetlab/2012/07/google-glass-theft-detection-system-gets-patented-future-nerds-rejoice/?goback=%2Egde_4437607_member_135570982.

International Preliminary Report on Patentability and Written Opinion of the International Searching Authority, "Headset Computer With Handsfree Emergency Response", dated Jan. 27, 2015 in corresponding PCT/US2013/051045.

\* cited by examiner

US 9,351,141 B2

HEADSET COMPUTER WITH HANDSFREE EMERGENCY RESPONSE

RELATED APPLICATION(S)

This application claims the benefit of U.S. Provisional Application No. 61/675,546, filed on Jul. 25, 2012. The entire teachings of the above application(s) are incorporated herein by reference.

BACKGROUND OF THE INVENTION

Mobile computing devices, such as notebook PC's, smart phones, and tablet computing devices, are now common tools used for producing, analyzing, communicating, and consuming data in both business and personal life. Consumers continue to embrace a mobile digital lifestyle as the ease of access to digital information increases with high-speed wireless communications technologies becoming ubiquitous. Popular uses of mobile computing devices include displaying large amounts of high-resolution computer graphics information and video content, often wirelessly streamed to the device. While these devices typically include a display screen, the preferred visual experience of a high-resolution, large format display cannot be easily replicated in such mobile devices because the physical size of such devices is limited to promote mobility. Another drawback of the aforementioned device types is that the user interface is hands-dependent, typically requiring a user to enter data or make selections using a keyboard (physical or virtual) or touch-screen display. As a result, consumers are now seeking a hands-free high-quality, portable, color display solution to augment or replace their hands-dependent mobile devices.

SUMMARY OF THE INVENTION

The present disclosure relates to a headset computer that determines when an individual may be wearing the headset computer while in a potentially unsafe or personally hostile environment. If the condition is detected, one or more security features are enabled.

A headset computer (HSC) includes one or more sensors to detect a threatening situation such as a personal assault, a camera, microphone, and sensors, such as an acceleration sensor and location sensor as well as user interface functions such as speech recognition, speech analysis, and gesture recognition.

In one implementation, a special spoken statement and/or hand gesture activates an emergency response mode. In this emergency response mode, the HSC activates certain special features such as turning on the microphone and/or camera to record audio and/or video, activating a silent wireless call to alert a service provider and/or emergency authorities, or more sophisticated functions such as broadcasting the recorded audio and/or video, broadcasting detected biometrics and/or location information concerning the emergency event detected in the vicinity of the HSC. Streaming of audio/video instead of broadcasting may be employed as an alternative.

In this mode, the HSC may be used to remotely control a hostile person's own wireless device to obtain further information such as their personal identification, contacts, calls and emails, etc.

These special emergency features permit a service provider or emergency responders to track and determine the location of the HSC, record and document the incident for further follow up with law enforcement officials, and/or to support other appropriate responses to a personal assault.

These features are generally preferred to operate in such a way that a hostile person attacking the owner of the HSC is not made aware that the special features have been activated.

More particularly, consider a situation where someone attempts to remove a headset computer from its owner. This generally means that the owner is in a hostile environment or a confrontation, possibly in the process of being robbed much as has become common with thugs stealing a person's cell phone. For clarification, hereinafter, the original/rightful user is referred to as a "user" and a thief/un-rightful user is referred to as "thief."

If the thief is looking for the immediate gratification of using the device but the device is itself shutdown or rendered inoperable in any way, the thief is likely to become upset and the likely outcome would be the thief either breaking the device or possibly harming the owner. The approach here is to permit the use of a special user-known statement (password) or a set of gestures to activate an emergency response mode. In this mode a number of features are silently activated.

A silent call may be made to 911 emergency responders.

The camera may be turned on to capture biometrics on every face it sees, or to store or broadcast live (real time) streaming video to the wireless service provider call center and/or police.

The microphone may be turned on to capture biometrics on every voice that it hears, or to store or to broadcast live streaming audio to the wireless service provider call center and/or police.

The GPS and/or other location sensors may transmit location information directly to the service provider call center and/or the police.

The approach allows the owner of the HSC to give control over their device, flee the situation with as little stress and bodily harm as possible, and allow the technology, the wireless service provider and the police to take care of the situation.

The emergency response mode may also permit remote control over all of the HSC's capabilities without the thief noticing. For example, with a warrant in hand, law enforcement personnel may operate the stolen HSC to scan the vicinity for other wireless devices, and pair to them to exercise remote control over them. Data may then be copied from the thief's paired wireless device, such as a telephone call history, text messages, emails, contact lists, etc., to further assist with apprehending criminals.

A further remoting function may be activated via passwords that may be remotely transmitted to the HSC to override passwords or speech recognition settings, etc. activated by the thief after the device is stolen and the emergency event has subsided. In this way, all HSC functionality is brought under the service provider, police or user's remote control. The HSC will continue to operate in the field, and the thief who stole the headset is basically prevented from stopping the HSC from being remotely monitored and controlled, as long as the device is powered on.

The HSC may also perform wireless connectivity scans, e.g., WiFi and Bluetooth resources scans, to identify Bluetooth and WiFi devices and resources in the immediate vicinity of the stolen HSC. This additional information may be used to further track, locate and improve the ability to recover lost and stolen headsets.

In addition, a "wireless computing headset" device includes one or more small high-resolution micro-displays and optics to magnify the image. The WVGA microdisplay's may provide super video graphics array (SVGA) (800×600) resolution or extended graphic arrays (XGA) (1024×768) or even higher resolutions. A wireless computing headset contains one or more wireless computing and communication interfaces, enabling data and streaming video capability, and provides greater convenience and mobility than hands dependent devices. For more information concerning such devices, see co-pending U.S. application Ser. No. 12/348,646 entitled "Mobile Wireless Display Software Platform for Controlling Other Systems and Devices," by Jacobsen et al., filed Jan. 5, 2009, PCT International Application No. PCT/US09/38601 entitled "Handheld Wireless Display Devices Having High Resolution Display Suitable For Use as a Mobile Internet Device," filed Mar. 27, 2009, and U.S. Application No. 61/638,419 entitled "Improved Headset Computer," filed Apr. 25, 2012, each of which are incorporated herein by reference in their entirety.

The proposed approach includes a method of controlling operation of a headset computer comprising: receiving a certain input from an original user, indicative of an impending emergency situation; in response to the received certain input from the original user, activating an emergency response mode whereby standard headset computer functions remain active for use by either the original user or an alternate user, but one or more functions are also performed as follows:

capturing at least one of an audio or video stream (live data);

comparing a captured image against one or more template images to determine image biometric identification data of one or more persons in the vicinity;

determining current location information; and forwarding at least one of the captured audio or video stream data, the determined biometric identification data, or the determined location information to at least one of a service provider, law enforcement agency, or security organization.

The proposed approach further includes a method wherein the one or more functions further include comparing a captured voice audio data against one or more template voices to determine voice biometric identification data of the one or more persons in the vicinity. The proposed approach further includes a method wherein the one or more functions further include identifying one or more wireless devices within a given (predefined threshold) proximity of the headset computer. The proposed approach further automatically pairs the headset computer with at least one of the identified one or more wireless devices. The proposed approach further includes a method wherein the one or more functions further include copying personal information from paired ones of the identified one or more wireless devices. The proposed approach further includes a method wherein the one or more functions further include overriding any password changes made by the alternate user.

The proposed approach further includes a method wherein the received certain input from the original user includes a spoken phrase, head movement, or hand gesture. The proposed approach further includes a method wherein the received certain input from the original user includes an image, sound, geographical position, general position, orientation, atmospheric condition, pressure, health condition, environment, energy, acceleration, altitude, motion, velocity, speed, or light including visible light, infrared light and ultraviolet light. The proposed approach further includes a method wherein the one or more functions are performed in a clandestine manner, such that the alternate user is unaware that the one or more functions are performed.

The proposed approach includes a device that controls operation of a headset computer comprising: a receiving unit that receives a certain input from an original user, indicative of an impending emergency situation; a response activation unit, that in response to the received certain input from the original user, activates an emergency response mode whereby standard headset computer functions remain active, for use by either the original user or an alternate user, and performs one or more functions as follows:

captures at least one of an audio or video stream/data;

compares a captured image against one or more template images to determine image biometric identification data of one or more persons in the vicinity;

determines location information; and forwards at least one of the captured audio or video stream, the determined biometric identification data, or the location information to at least one of a service provider, law enforcement agency, or security organization.

The proposed approach further includes a device wherein the response activation unit compares a captured voice data against one or more template voices to determine voice biometric identification data of the one or more persons in the vicinity. The proposed approach further includes a device wherein the response activation unit identifies one or more wireless devices within a given (predefined) proximity of the headset computer.

The proposed approach further includes a device wherein the response activation unit automatically pairs the headset computer with at least one of the identified one or more wireless devices. The proposed approach further includes a device wherein the response activation unit copies personal information from the paired ones of the identified one or more wireless devices. The proposed approach further includes a device wherein the response activation unit overrides any password changes made by the alternate user.

The proposed approach further includes a device wherein the received certain input from the original user includes a spoken phrase, head movement, or hand gesture. The proposed approach further includes a device wherein the received certain input from the original user includes a sound, geographical position, general position, orientation, atmospheric condition, pressure, health condition, environment, energy, acceleration, altitude, motion, velocity, speed, or light including visible light, infrared light and ultraviolet light. The proposed approach further includes a device wherein the one or more functions are performed in a clandestine manner by the response activation unit, such that the alternate user is unaware that the one or more functions are performed.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF THE INVENTION

Figure 1A:
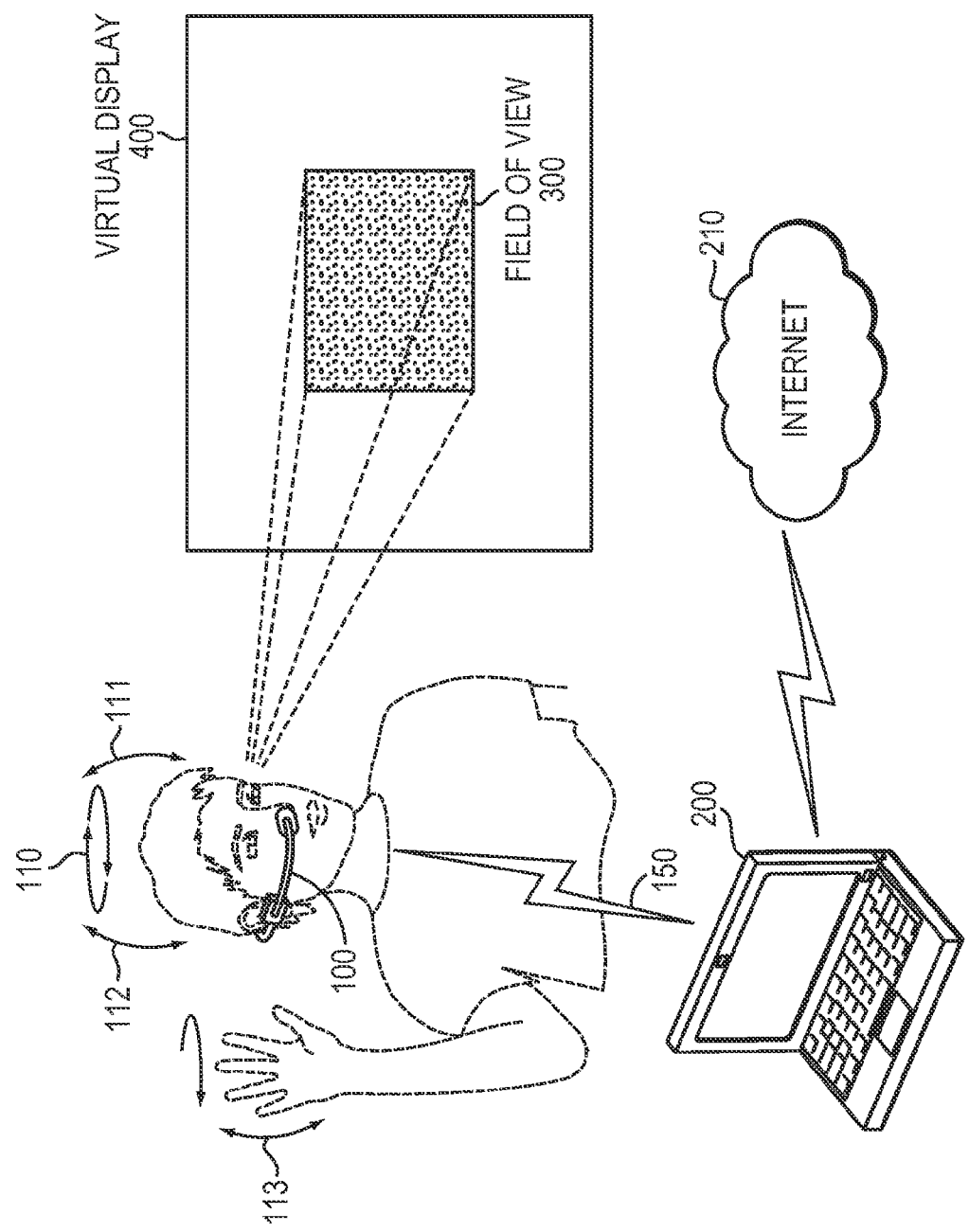
FIG. 1A illustrates example embodiments of a headset computer and a headset computer cooperating with a host computer (e.g., Smart Phone, laptop, etc.) according to principles of the present invention.
Figure 1B:
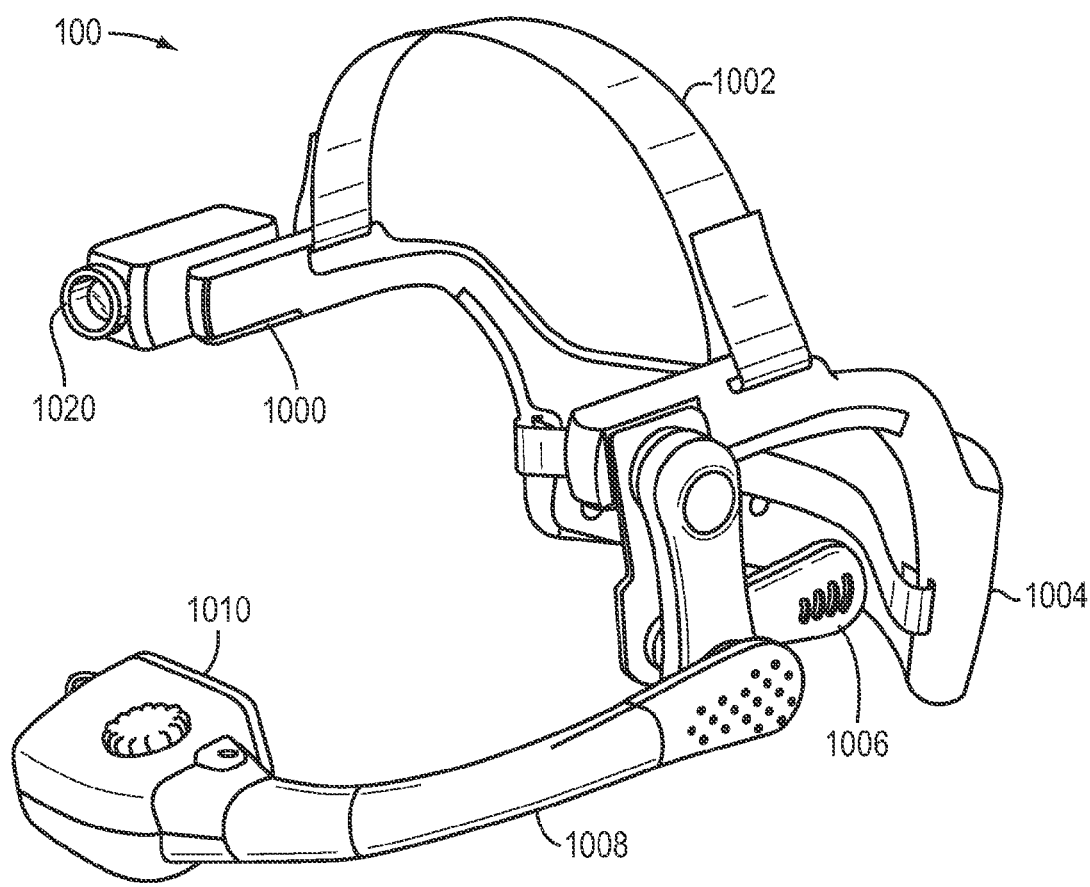
FIG. 1B is a perspective view of one type of headset computer in which the approaches described herein may be implemented.

FIGS. 1A and 1B show an example embodiment of a wireless computing headset or head-mounted device 100 (also referred to herein as a headset computer (HSC)) that incorporates a high-resolution (VGA or better) microdisplay element 1010, and other features described below. A HSC 100 may include audio input and/or output devices, including one or more microphones, speakers, geo-positional sensors (GPS), three to nine axis degrees of freedom orientation sensors, atmospheric sensors, health condition sensors, digital compass, pressure sensors, environmental sensors, energy sensors, acceleration sensors, position, attitude, motion, velocity and/or optical sensors, cameras (visible light, infrared, etc.), multiple wireless radios, auxiliary lighting, rangefinders, or the like and/or an array of sensors embedded and/or integrated into the headset and/or attached to the device via one or more peripheral ports (not shown in detail in FIG. 1B). Typically located within the housing of headset computing device 100 are various electronic circuits including, a microcomputer (single or multicore processors), one or more wired and/or wireless communications interfaces, memory or storage devices, various sensors and a peripheral mount, such as a "hot shoe" at 1020.

Example embodiments of the HSC 100 may receive user input through sensing voice commands, head movements, 110, 111, 112 and hand gestures 113, or any combination thereof. Microphone(s) operatively coupled or preferably integrated into the HSC 100 may be used to capture speech commands which are then digitized and processed using automatic speech recognition techniques. Gyroscopes, accelerometers, and other micro-electromechanical system sensors may be integrated into the HSC 100 and used to track the user's head movement to provide user input commands. Cameras 1020 or other motion tracking sensors may be used to monitor a user's hand gestures for user input commands. Such a user interface overcomes the hands-dependant formats of other mobile devices.

The headset computing device 100 may be used in various ways. It may be used as a remote display for streaming video signals received from a remote host computing device 200 (shown in FIG. 1A). The host 200 may be, for example, a laptop, notebook PC, cell phone, smart phone, tablet device, another HSC 100 or other computing device having less or greater computational complexity than the wireless computing headset device 100, such as cloud-based network resources. The host may be further connected to other networks 210, such as the Internet. The headset computing device 100 and host 200 may wirelessly communicate via one or more wireless protocols, such as Bluetooth®, Wi-Fi®, cellular, LTE, WiMAX or other wireless radio link 150. (Bluetooth is a registered trademark of Bluetooth Sig, Inc. of 5209 Lake Washington Boulevard, Kirkland, Wash. Wi-Fi is a registered trademark of Wi-Fi Alliance Corporation of Austin, Tex.) In an example embodiment, the host 200 may be further connected to other networks, such as through a wireless connection to the Internet or other cloud-based network resources, so that the host 200 may act as a wireless relay. Alternatively, some example embodiments of the HSC 100 may wirelessly connect to the Internet and cloud-based network resources without the use of a host wireless relay.

FIG. 1B is a perspective view showing some details of an example embodiment of a headset computer 100. The example HSC 100 generally includes a frame 1000, strap 1002, housing section 1004, speaker(s) 1006, cantilever or arm 1008, microdisplay subassembly 1010, and camera 1020. Also located within the housing 1004 are various electronic circuits including, as will be understood shortly, a microcomputer (single or multi-core), one or more wired or wireless interfaces, and/or optical interfaces, associated memory and/or storage devices, and various sensors.

The electronic circuits include display drivers for the microdisplay element 1010 and input and/or output devices, such as one or more microphone(s), speaker(s), geo-position sensors, 3 axis to 9 axis degrees of freedom orientation sensing, atmospheric sensors, health condition sensors, GPS, digital compass, pressure sensors, environmental sensors, energy sensors, acceleration, position, altitude, motion, velocity or optical sensors, cameras (visible light, infrared (IR), ultra violet (UV), etc.), additional wireless radios (Bluetooth®, Wi-Fi®, LTE, 3G Cellular, 4G Cellular, NFC, FM, etc.), auxiliary lighting, range finders, or the like, and/or an array of sensors embedded in the headset frame and/or attached via one or more peripheral ports. (Bluetooth is a registered trademark of Bluetooth Sig, Inc., of Kirkland Wash.; and Wi-Fi is a registered trademark of Wi-Fi Alliance Corporation of Austin Tex.)

The HSC may be embodied in various physical forms such as a head mounted computer as shown, but also as a wearable computer, digital eyewear, electronic eyeglasses, and in other forms.

Also located within HSC 100 are circuits including, as will be understood shortly, a microcomputer (single or multi-core), one or more wireless interfaces, associated memory or other storage devices, one or more cameras (optical sensors) and/or various sensors previously mentioned. The camera(s) 1020, motion sensor(s) and/or positional sensor(s) are used to track the motion and/or position of the user's head, hands and/or body in at least a first axis 110 (horizontal), but preferably also a second (vertical) 112, third (depth) 113, fourth (pitch), fifth (roll) and sixth (yaw). A three axis magnetometer (digital compass) may be added to provide the wireless computing headset or peripheral device with a full 9-axis degrees of freedom position accuracy.

The HSC 100 also includes at least one microphone and corresponding electronics and/or programmable processors for speech recognition. Speech may be a primary input interface to the HSC 100, which is capable of detecting a user's voice, detecting a voice that is different from the user's, and using speech recognition to derive commands. The HSC 100 then uses the commands derived from the speech recognition to perform various functions.

Various types of accessories may be used with the port at 1020 to provide the hand movements, head movements, and or vocal inputs to the system, such as but not limited to microphones, positional, orientation and other previously described sensors, cameras, speakers, and the like. It should be recognized that the location of the periphery port (or ports), such as at 1020 may be varied according to the various types of accessories to be used and with other embodiments of the HSC 100.

A head worn frame 1000 and strap 1002 are generally configured so that a user may wear the headset computer device 100 on the user's head. A housing 1004 generally houses the electronics, such as the microprocessor, memory or other storage device, low power wireless communications device(s), along with other associated circuitry. Speakers 1006 provide audio output to the user so that the user may hear information, such as the audio portion of a multimedia presentation, or audio alert or feedback signaling recognition of a user command. Microdisplay subassembly 1010 is used to render visual information to the user. It is coupled to the arm 1008. The arm 1008 generally provides physical support such that the microdisplay subassembly is able to be positioned within the user's field of view 300 (FIG. 1A), preferably in front of the eye of the user or within its peripheral vision preferably slightly below or above the eye. Arm 1008 also provides the electrical or optical connections between the microdisplay subassembly 1010 and the control circuitry housed within housing unit 1004.

According to aspects that will be explained in more detail below, the HSC display device 100 allows a user to select a field of view 300 within a much larger area defined by a virtual display 400. The user may typically control the position, extent (e.g., X-Y or 3D range), and/or magnification of the field of view 300.

While what is shown in FIGS. 1A-1B are HSCs 100 with monocular microdisplays presenting a single fixed display element supported within the field of view in front of the face of the user with a cantilevered boom, it should be understood that other mechanical configurations for the remote control display device HSC 100 are possible.

Figure 2A:
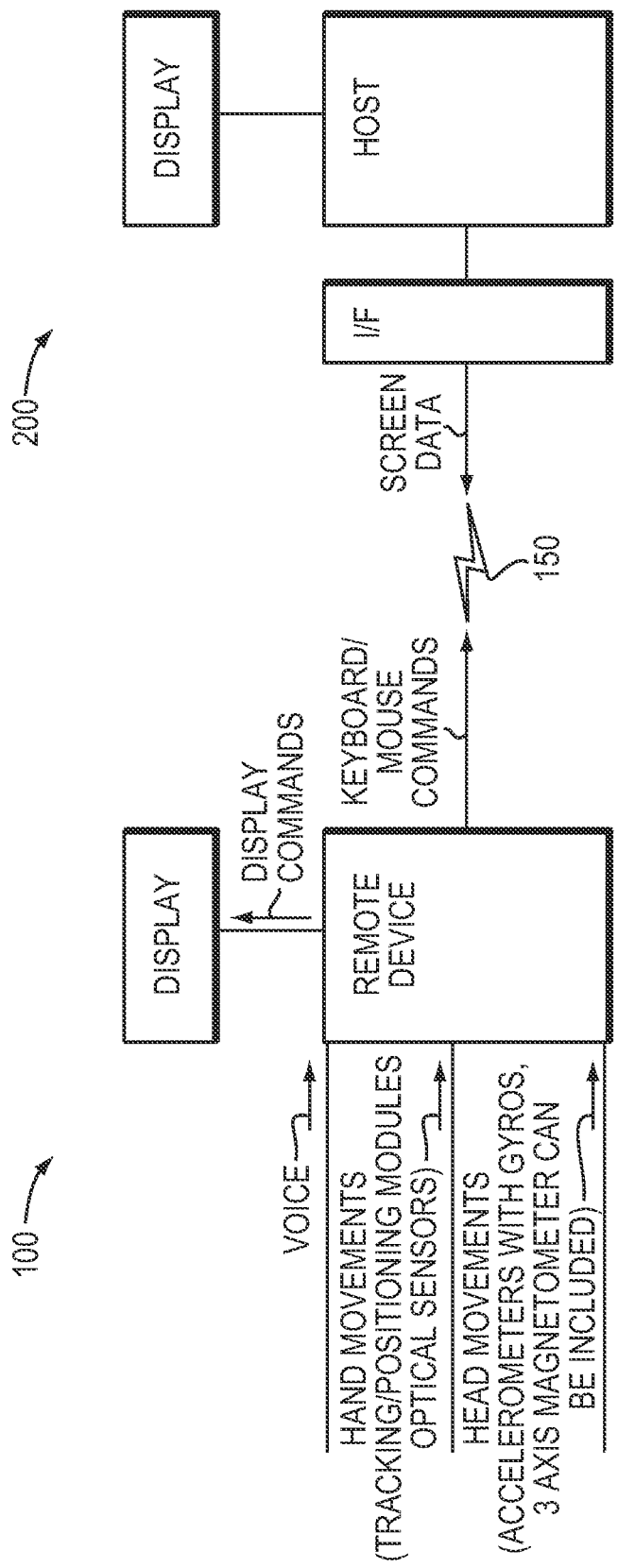
FIG. 2A is a block diagram of flow of data and control in the embodiment of FIGS. 1A-1B.

FIG. 2A is a block diagram showing more detail of the HSC device 100, host 200 and the data that travels between them. The HSC device 100 receives vocal input from the user via the microphone, hand movements or body gestures via positional and orientation sensors, the camera 1020 or optical sensor(s), and head movement inputs via the head tracking circuitry such as 3 axis to 9 axis degrees of freedom orientational sensing. These user inputs are translated by software in the HSC device 100 into commands (e.g., keyboard and/or mouse commands) that are then sent over the Bluetooth or other wireless interface 150 to the host 200. The host 200 then interprets these translated commands in accordance with its own operating system/application software to perform various functions. Among the commands is one to select a field of view 300 within the virtual display 400 and return that selected screen data to the HSC device 100. Thus, it should be understood that a very large format virtual display area might be associated with application software or an operating system running on the host 200. However, only a portion of that large virtual display area 400 within the field of view 300 is returned to and actually displayed by the micro display 1010 of HSC device 100.

In one embodiment, the HSC 100 may take the form of the HSC described in Applicant's co-pending U.S. Patent Publication No. 2011/0187640 (which is U.S. patent application Ser. No. 13/018,999) entitled "Wireless Hands-Free Computing Headset With Detachable Accessories Controllable By Motion, Body Gesture And/Or Vocal Commands" by S. Pombo et al. filed Feb. 1, 2011, which is hereby incorporated by reference in its entirety.

In another example embodiment, the invention relates to the concept of using a HSC (or Head Mounted Display (HMD)) 100 with microdisplay 1010 in conjunction with an external 'smart' device 200 (such as a smartphone or tablet) to provide information and hands-free user control. The embodiment requires transmission of small amounts of data, providing a more reliable data transfer method running in real-time.

In this sense therefore, the amount of data to be transmitted over the wireless connection 150 is small—simply instructions on how to lay out a screen, which text to display, and other stylistic information such as drawing arrows, or the background colours, images to include, etc.

Figure 2B:
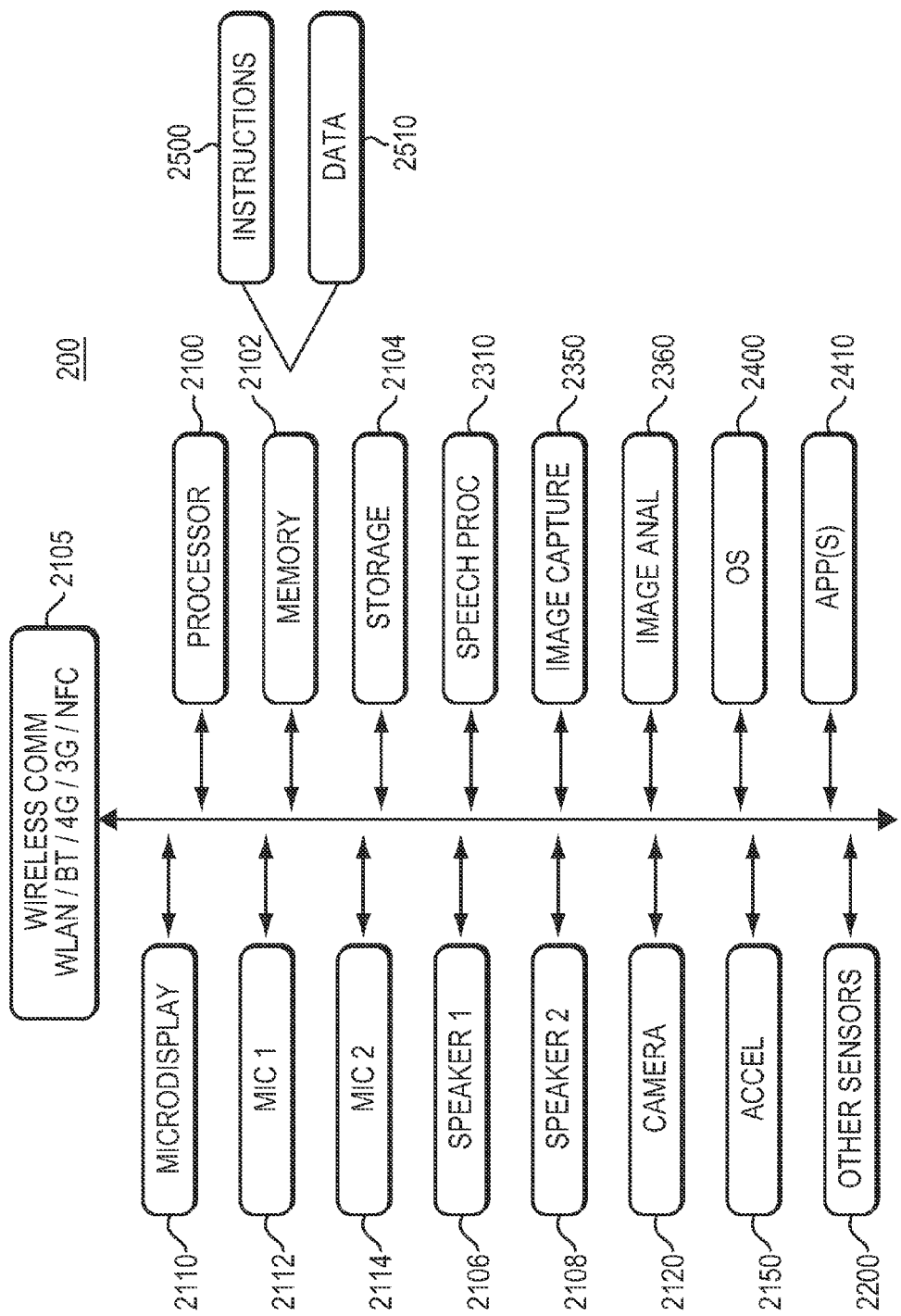
FIG. 2B is a high-level electronic system block diagram of the components of the headset computer.

FIG. 2B is a high-level electronic system block diagram of the components of the headset computer 100. As shown these include a processor 2100, memory 2102, and mass storage 2104 as with any programmable digital computer system. Also included are the microdisplay 2110, one or more microphones 2112, 2114, speakers 2106, 2108, and wireless communication interface(s) 2105.

Of importance to the present disclosure is that the HSC 100 also includes a camera 2120 and an accelerometer 2150 or other sensors 2200 such as Global Position System (GPS) sensors that may deliver current location information, movement direction information, and/or speed information.

To detect when an emergency response mode should be activated by the HSC 100, the processor executes instructions 2500 and accesses data 2510 stored by the memory 2102 and/or other storage 2104. The processor 2100 may for example execute instructions embodied as software code. The processor 2100 may also make use of an operating system 2400 and applications 2410 running within the context of the operating system 2400 to provide various functions.

Of interest here is that the processor also executes stored instructions 2500 to perform speech processing 2310, image capture 2350 and/or image analysis 2360. The speech processing 2310, image capture 2350 and image analysis 2360 preferably occur in real time and therefore are preferably implemented as low-level system calls, or even kernel-level functions in the operating system 2400. But in some instances these may also be implemented as applications 2410 running on top of the operating system 2400.

More particularly, the processor is programmed to automatically use the speech recognition, image capture 2350 and/or image analysis functions 2360 to determine when a superior or threatening force may be attacking the wearer of the HSC 100, and or attempting to steal the HSC 100, and to activate an emergency response mode. In this mode, the general notion is that the HSC 100 will continue to appear to operate normally, but will in reality be performing certain background functions. This allows the wearer of the HSC 100 to give up proximal control over their device, flee the situation with as little risk to their personal safety as possible, while at the same time permitting the technology embedded in the device to assist with responding to the event.

Figure 3:
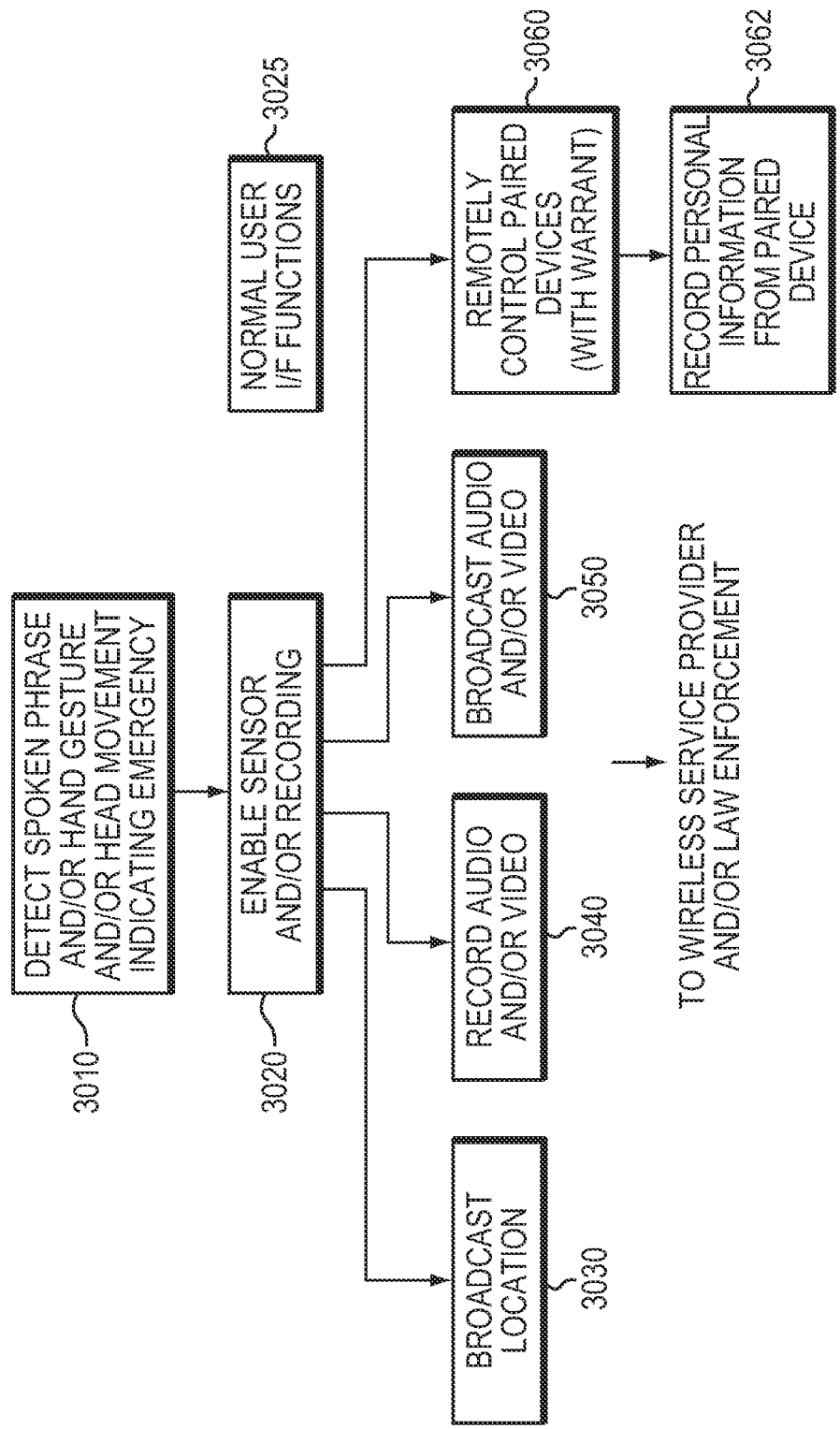
FIG. 3 is a flow diagram of a process executed by a processor in the headset to control operation when an emergency response situation is detected.

FIG. 3 is a flow diagram of an emergency response process that may be executed by the processor 2100. In a first step 3010 a certain (predefined) spoken phrase and/or head or hand gesture(s) is detected indicating an emergency situation. The spoken phrase may be a special pass phrase or keyword that the user has set in advance to indicate that he has encountered a situation that compromises his personal safety, such as being confronted by a thief who is attempting to steal the HSC 100. Alternatively predefined head and/or hand gestures may also be used to activate the emergency response mode.

Such voice commands are detected by the microphone(s) 2112, 2114 and interpreted by the speech processor 2310. In the event of the certain input being a head and/or hand gesture(s), this is initially detected by the image capture 2350 and then further detected/determined through image analysis 2360. In addition, head gesture(s) may be initially detected by a pre-defined change in orientation, through orientation sensors 2200. Other examples of the certain input include: a geographical position; a general position; orientation; indication of an atmospheric condition, pressure, or a health condition; indication of environment; an energy, acceleration, altitude, motion, light or speed/velocity reading by sensors 2200.

Entering the emergency response mode causes a number of things to happen. In step 3020, additional sensors and/or recording functions are enabled. In the meantime, in step 3025, normal user interface functions continue. This is so that even when the emergency mode is entered, all normal operational capabilities of the HSC 100 may remain activated, for the thief to use, without notification to the potential hostile person, thief, who is not otherwise tipped off that the special mode has been activated.

Upon enabling the sensors and/or recording apparatus various further functions may be performed. In addition to the functionality of step 3020, one or more of the steps 3025, 3030, 3040, 3050, 3060, 3062 may be performed, simultaneously, or otherwise.

For example, in step 3030 location information is broadcast and available via the onboard GPS and/or digital compass.

In step 3040, audio and/or video is recorded through the camera and microphone(s).

In step 3050, the recorded audio and/or video stream (or data) is broadcast.

The broadcast in step 3030 or 3050 may be to a wireless service provider or law enforcement or may be indirectly to law enforcement through the wireless service provider.

Thus in an emergency situation the owner of the HSC 100 may give up physical control over the HSC 100 rapidly and run away from the situation to minimize bodily harm to himself. In the meantime, the HSC 100 enters clandestine recording and reporting functions in the emergency response mode, sampling and recording surrounding voices, photographing faces during the confrontation or attempted robbery, detecting and broadcasting biometrics on each person's face and/or voice captured while also broadcasting its location and compass heading.

The wireless service provider may then pass through this (relay) information to law enforcement officials so that they may listen into the live and/or recorded audio and/or video streams to attempt to retrieve the stolen headset and apprehend suspect(s) for prosecuting any ensuing assault or personal injury may have occurred.

With this information, it may also be possible for law enforcement to obtain a search warrant. With the warrant in hand, further functions of the HSC 100 may be utilized. In an example step 3060, the HSC 100 may act as a remote control over other wireless devices in the vicinity of the thief. The HSC 100 may pair to other wireless devices, mobile phones, personal computers and the like and record/copy 3062 information about the thief, his contact lists, his past telephone calls, e-mails, text messages, and the like, all of which may further assist law enforcement.

A further remoting function may be activated via passwords that may be remotely transmitted to the HSC to override passwords or speech recognition settings, etc. activated by the thief after the device has been stolen and the emergency event has subsided. In this way, all HSC functionality is brought under the service provider, police or user's remote control. The thief who stole the headset thus cannot easily stop the HSC from being remotely monitored and controlled, as long as power is applied to the HSC.

The HSC may also perform wireless connectivity scans, e.g., WiFi and Bluetooth resources scans, to identify Bluetooth and WiFi devices and resources in the immediate vicinity of the stolen HSC. This additional information may be used to further track, locate and improve the ability to recover lost and stolen headsets.

It should be understood that the example embodiments described above may be implemented in many different ways. In some instances, the various "data processors" described herein may each be implemented by a physical or virtual general purpose computer having a central processor, memory, disk or other mass storage, communication interface(s), input/output (I/O) device(s), and other peripherals.

The general purpose computer is transformed into the processors and executes the processes described above, for example, by loading software instructions into the processor, and then causing execution of the instructions to carry out the functions described.

As is known in the art, such a computer may contain a system bus, where a bus is a set of hardware lines used for data transfer among the components of a computer or processing system. The bus or busses are essentially shared conduit(s) that connect different elements of the computer system (e.g., processor, disk storage, memory, input/output ports, network ports, etc.) that enables the transfer of information between the elements. One or more central processor units are attached to the system bus and provide for the execution of computer instructions. Also attached to system bus are typically I/O device interfaces for connecting various input and output devices (e.g., keyboard, mouse, displays, printers, speakers, etc.) to the computer. Network interface(s) allow the computer to connect to various other devices attached to a network. Memory provides volatile storage for computer software instructions and data used to implement an embodiment. Disk or other mass storage provides non-volatile storage for computer software instructions and data used to implement, for example, the various procedures described herein.

Embodiments may therefore typically be implemented in hardware, firmware, software, or any combination thereof.

In certain embodiments, the procedures, devices, and processes described herein are a computer program product, including a computer readable medium (e.g., a removable storage medium such as one or more DVD-ROM's, CD-ROM's, diskettes, tapes, etc.) that provides at least a portion of the software instructions for the system. Such a computer program product may be installed by any suitable software installation procedure, as is well known in the art. In another embodiment, at least a portion of the software instructions may also be downloaded over a cable, communication and/or wireless connection.

Embodiments may also be implemented as instructions stored on a non-transient machine-readable medium, which may be read and executed by one or more procedures. A non-transient machine-readable medium may include any mechanism for storing or transmitting information in a form readable by a machine (e.g., a computing device). For example, a non-transient machine-readable medium may include read only memory (ROM); random access memory (RAM); storage including magnetic disk storage media; optical storage media; flash memory devices; and others.

Furthermore, firmware, software, routines, or instructions may be described herein as performing certain actions and/or functions. However, it should be appreciated that such descriptions contained herein are merely for convenience and that such actions in fact result from computing devices, processors, controllers, or other devices executing the firmware, software, routines, instructions, etc.

It also should be understood that the block and network diagrams may include more or fewer elements, be arranged differently, or be represented differently. But it further should be understood that certain implementations may dictate the block and network diagrams and the number of block and network diagrams illustrating the execution of the embodiments be implemented in a particular way.

Accordingly, further embodiments may also be implemented in a variety of computer architectures, physical, virtual, cloud computers, and/or some combination thereof, and thus the computer systems described herein are intended for purposes of illustration only and not as a limitation of the embodiments.

Therefore, while this invention has been particularly shown and described with references to example embodiments thereof, it will be understood by those skilled in the art that various changes in form and details may be made therein without departing from the scope of the invention encompassed by the appended claims.

The teachings of all patents, published applications and references cited herein are incorporated by reference in their entirety.

What is claimed is:

1. A method of controlling operation of a headset computer comprising:
    receiving a hands-free gesture input from an original user, exclusively indicative of an impending emergency situation;
    in response to the received certain input from the original user, activating an emergency response mode whereby standard headset computer functions remain active for use by either the original user or an alternate user, but the following actions are also performed:
    capturing at least one of an audio or video stream, the capturing occurring as a result of entering the emergency response mode, without requiring a user input specifically associated with capturing one or more of the audio or video stream;
    determining location information;
    identifying one or more wireless devices within a proximity of the headset computer, automatically pairing the headset computer with at least one of the identified one or more wireless devices, and copying personal information from paired ones of the identified one or more wireless devices; and
    forwarding at least one of the captured audio or video stream, the copied personal information, and the location information to at least one of a service provider, law enforcement agency, or security organization.

2. The method of claim 1, wherein the one or more functions further include comparing a captured voice audio data against one or more template voices to determine voice biometric identification data of the one or more persons in the vicinity.

3. The method of claim 1, further including comparing a captured image against one or more template images to determine image biometric identification data of one or more persons in the vicinity, and forwarding the determined biometric identification data.

4. The method of claim 1, wherein the one or more functions further include overriding any password changes made by the alternate user.

5. The method of claim 1, wherein the received certain input from the original user includes a spoken phrase, head movement, or hand gesture.

6. The method of claim 1, wherein the received certain input from the original user includes an image, sound, geographical position, general position, orientation, atmospheric condition, pressure, health condition, environment, energy, acceleration, altitude, motion, velocity, speed, or light including visible light, infrared light and ultraviolet light.

7. The method of claim 1, wherein the one or more functions are performed in a clandestine manner, such that the alternate user is not notified that the one or more functions are performed.

8. A device that controls operation of a headset computer comprising:
    a receiving unit that receives a hands-free gesture input from an original user, exclusively indicative of an impending emergency situation;
    a response activation unit configured to, in response to the received certain input from the original user, activate an emergency response mode whereby standard headset computer functions remain active, for use by either the original user or an alternate user, and perform the following actions:
    capture at least one of an audio or video stream, without requiring a user input specifically associated with capturing one or more of the audio or video stream;
    determine location information;
    identify one or more wireless devices within a proximity of the headset computer, automatically pair the headset computer with at least one of the identified one or more wireless devices, and copy personal information from paired ones of the identified one or more wireless devices; and
    forward at least one of the captured audio or video stream, the copied personal information, and the location information to at least one of a service provider, law enforcement agency, or security organization.

9. The device of claim 8, wherein the response activation unit compares a captured voice audio data against one or more template voices to determine voice biometric identification data of the one or more persons in the vicinity.

10. The device of claim 8, wherein the response activation unit further compares a captured image against one or more template images to determine image biometric identification data of one or more persons in the vicinity, and forwarding the determined biometric identification data.

11. The device of claim 8, wherein the response activation unit overrides any password changes made by the alternate user.

12. The device of claim 8, wherein the received certain input from the original user includes a spoken phrase, head movement, or hand gesture.

13. The device of claim 8, wherein the received certain input from the original user includes an image, sound, geographical position, general position, orientation, atmospheric condition, pressure, health condition, environment, energy, acceleration, altitude, motion, velocity, speed, or light including visible light, infrared light and ultraviolet light.

14. The device of claim 8, wherein the response activation unit performs the one or more functions in a clandestine manner, such that the alternate user is not notified that the one or more functions are performed.

* * * * *